United States Patent
Mazar et al.

(10) Patent No.: US 7,751,901 B2
(45) Date of Patent: Jul. 6, 2010

(54) ADVANCED PATIENT MANAGEMENT SYSTEM INCLUDING INTERROGATOR/TRANSCEIVER UNIT

(75) Inventors: Scott Thomas Mazar, Inver Grove Heights, MN (US); Yatheendhar D. Manicka, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 589 days.

(21) Appl. No.: 11/259,938

(22) Filed: Oct. 26, 2005

(65) Prior Publication Data

US 2006/0106433 A1    May 18, 2006

Related U.S. Application Data

(63) Continuation of application No. 10/330,677, filed on Dec. 27, 2002, now Pat. No. 6,978,182.

(51) Int. Cl.
*A61N 1/00* (2006.01)
(52) U.S. Cl. .......................................... 607/60
(58) Field of Classification Search .................. 607/30, 607/31, 60; 455/41.2; 600/559
See application file for complete search history.

(56) References Cited

U.S. PATENT DOCUMENTS

| | | | |
|---|---|---|---|
| 4,305,397 A * | 12/1981 | Weisbrod et al. .............. 607/30 |
| 4,561,443 A | 12/1985 | Hogrefe et al. |
| 4,658,831 A | 4/1987 | Reinhard et al. |
| 4,681,111 A | 7/1987 | Silvian |
| 4,705,043 A | 11/1987 | Imran |
| 4,757,816 A | 7/1988 | Ryan et al. |
| 4,793,353 A | 12/1988 | Borkan |
| 4,809,697 A | 3/1989 | Causey, III et al. |
| 4,932,408 A | 6/1990 | Schaldach |
| 4,941,201 A * | 7/1990 | Davis ........................ 455/41.2 |
| 4,947,407 A | 8/1990 | Silvian |
| 4,969,464 A | 11/1990 | Callaghan et al. |
| 5,058,581 A | 10/1991 | Silvian |
| 5,081,987 A | 1/1992 | Nigam |
| 5,113,869 A | 5/1992 | Nappholz et al. |
| 5,117,825 A | 6/1992 | Grevious |
| 5,137,022 A | 8/1992 | Henry |
| 5,241,961 A | 9/1993 | Henry |
| 5,292,343 A | 3/1994 | Blanchette et al. |
| 5,331,966 A | 7/1994 | Bennett et al. |
| 5,336,245 A | 8/1994 | Adams et al. |
| 5,350,411 A | 9/1994 | Ryan et al. |

(Continued)

FOREIGN PATENT DOCUMENTS

EP    0554955 A1    8/1993

*Primary Examiner*—George Manuel
(74) *Attorney, Agent, or Firm*—Schwegman, Lundberg & Woessner, P.A.

(57) ABSTRACT

An advanced patient management system including at least one device that is implanted in a patient, the device being configured to measure physiological attributes of the patient and provide therapy to the patient. The advanced patient management system may also include an interrogator/transceiver unit in communication with the device and a network, the unit being positioned relative to the device to facility communication between the repeater and the device. The advanced patient management system also includes a host, in communication with the device through the network, to store data from the device and to provide a predictive diagnosis of an oncoming event. The interrogator/transceiver unit may include programmable or updateable with software from a computer system or remote host.

14 Claims, 6 Drawing Sheets

U.S. PATENT DOCUMENTS

| | | |
|---|---|---|
| 5,381,798 A | 1/1995 | Burrows |
| 5,383,915 A | 1/1995 | Adams |
| 5,413,594 A | 5/1995 | Williams |
| 5,415,181 A | 5/1995 | Hogrefe et al. |
| 5,456,692 A | 10/1995 | Smith, Jr. et al. |
| 5,458,122 A | 10/1995 | Hethuin |
| 5,476,485 A | 12/1995 | Weinberg et al. |
| 5,481,262 A | 1/1996 | Urbas et al. |
| 5,509,927 A | 4/1996 | Epstein et al. |
| 5,522,865 A | 6/1996 | Schulman et al. |
| 5,549,654 A | 8/1996 | Powell |
| 5,626,630 A | 5/1997 | Markowitz et al. |
| 5,629,678 A | 5/1997 | Gargano et al. |
| 5,630,836 A | 5/1997 | Prem et al. |
| 5,674,249 A | 10/1997 | De Coriolis et al. |
| 5,683,432 A | 11/1997 | Goedeke et al. |
| 5,713,937 A | 2/1998 | Nappholz et al. |
| 5,720,770 A | 2/1998 | Nappholz et al. |
| 5,741,315 A | 4/1998 | Lee et al. |
| 5,743,267 A | 4/1998 | Nikolic et al. |
| 5,752,976 A | 5/1998 | Duffin et al. |
| 5,752,977 A | 5/1998 | Grevious et al. |
| 5,759,199 A | 6/1998 | Snell et al. |
| 5,766,232 A | 6/1998 | Grevious et al. |
| 5,769,876 A | 6/1998 | Silvian |
| 5,772,586 A | 6/1998 | Heinonen et al. |
| 5,774,501 A | 6/1998 | Halpern et al. |
| 5,791,342 A | 8/1998 | Woodard |
| 5,792,207 A | 8/1998 | Dietrich |
| 5,814,089 A | 9/1998 | Stokes et al. |
| 5,836,983 A | 11/1998 | Weijand et al. |
| 5,843,133 A | 12/1998 | Routh et al. |
| 5,843,139 A | 12/1998 | Goedeke et al. |
| 5,861,014 A | 1/1999 | Familoni |
| 5,861,018 A | 1/1999 | Feierbach |
| 5,862,803 A | 1/1999 | Besson et al. |
| 5,889,474 A | 3/1999 | LaDue |
| 5,899,928 A | 5/1999 | Sholder et al. |
| 5,899,931 A | 5/1999 | Deschamp et al. |
| 5,907,491 A | 5/1999 | Canada et al. |
| 5,917,414 A | 6/1999 | Oppelt et al. |
| 5,919,214 A | 7/1999 | Ciciarelli et al. |
| 5,935,078 A | 8/1999 | Feierbach |
| 5,944,659 A | 8/1999 | Flach et al. |
| 5,957,861 A | 9/1999 | Combs et al. |
| 5,999,857 A | 12/1999 | Weijand et al. |
| 6,083,248 A | 7/2000 | Thompson |
| 6,093,146 A | 7/2000 | Filangeri |
| 6,115,636 A | 9/2000 | Ryan |
| 6,141,584 A | 10/2000 | Rockwell et al. |
| 6,170,488 B1 | 1/2001 | Spillman, Jr. et al. |
| 6,185,452 B1 | 2/2001 | Schulman et al. |
| 6,200,264 B1 | 3/2001 | Satherley et al. |
| 6,203,495 B1 | 3/2001 | Bardy |
| 6,206,835 B1 | 3/2001 | Spillman, Jr. et al. |
| 6,208,894 B1 | 3/2001 | Schulman et al. |
| 6,213,942 B1 | 4/2001 | Flach et al. |
| 6,216,038 B1 | 4/2001 | Hartlaub et al. |
| 6,221,011 B1 | 4/2001 | Bardy |
| 6,223,083 B1 | 4/2001 | Rosar |
| 6,236,889 B1 | 5/2001 | Soykan et al. |
| 6,240,317 B1 | 5/2001 | Villaseca et al. |
| 6,250,309 B1 | 6/2001 | Krichen et al. |
| 6,261,230 B1 | 7/2001 | Bardy |
| 6,263,245 B1 | 7/2001 | Snell et al. |
| 6,263,246 B1 | 7/2001 | Goedeke et al. |
| 6,263,247 B1 | 7/2001 | Mueller et al. |
| 6,289,238 B1 | 9/2001 | Besson et al. |
| 6,292,698 B1 | 9/2001 | Duffin et al. |
| 6,295,466 B1 | 9/2001 | Ishikawa et al. |
| 6,298,271 B1 | 10/2001 | Weijand |
| 6,300,903 B1 | 10/2001 | Richards et al. |
| 6,304,788 B1 | 10/2001 | Eady et al. |
| 6,312,378 B1 | 11/2001 | Bardy |
| 6,319,200 B1 | 11/2001 | Lai et al. |
| 6,329,929 B1 | 12/2001 | Weijand et al. |
| 6,345,203 B1 | 2/2002 | Mueller et al. |
| 6,349,234 B2 | 2/2002 | Pauly et al. |
| 6,363,282 B1 | 3/2002 | Nichols et al. |
| 6,418,346 B1 | 7/2002 | Nelson et al. |
| 6,442,432 B2 | 8/2002 | Lee |
| 6,477,242 B1 | 11/2002 | Freeny, Jr. et al. |
| 6,480,745 B2 | 11/2002 | Nelson et al. |
| 6,564,104 B2 * | 5/2003 | Nelson et al. ................ 607/60 |
| 6,635,014 B2 | 10/2003 | Starkweather et al. |
| 6,735,630 B1 | 5/2004 | Gelvin et al. |
| 2001/0023360 A1 | 9/2001 | Nelson et al. |
| 2001/0025137 A1 | 9/2001 | Webb et al. |
| 2001/0025189 A1 | 9/2001 | Haueter et al. |
| 2001/0027331 A1 | 10/2001 | Thompson |
| 2001/0027349 A1 | 10/2001 | Eady et al. |
| 2001/0029321 A1 | 10/2001 | Beetz et al. |
| 2001/0031998 A1 | 10/2001 | Nelson et al. |
| 2001/0037056 A1 | 11/2001 | Nunome |
| 2001/0039372 A1 | 11/2001 | Yasushi et al. |
| 2001/0044588 A1 | 11/2001 | Mault |
| 2001/0047125 A1 | 11/2001 | Quy |
| 2001/0049554 A1 | 12/2001 | Ruiz et al. |
| 2001/0051764 A1 | 12/2001 | Bardy |
| 2002/0013517 A1 | 1/2002 | West et al. |
| 2002/0013518 A1 | 1/2002 | West et al. |
| 2002/0013538 A1 | 1/2002 | Teller |
| 2002/0013613 A1 | 1/2002 | Haller et al. |
| 2002/0013614 A1 | 1/2002 | Thompson |
| 2002/0019584 A1 | 2/2002 | Schulze et al. |
| 2002/0019586 A1 | 2/2002 | Teller et al. |
| 2002/0028988 A1 | 3/2002 | Suzuki et al. |
| 2002/0032470 A1 | 3/2002 | Linberg |
| 2002/0040234 A1 | 4/2002 | Linberg |
| 2002/0052539 A1 | 5/2002 | Haller et al. |
| 2002/0072785 A1 | 6/2002 | Nelson et al. |
| 2002/0082665 A1 | 6/2002 | Haller et al. |
| 2002/0165466 A1 * | 11/2002 | Givens et al. ................ 600/559 |

* cited by examiner

ADVANCED PATIENT MANAGEMENT SYSTEM INCLUDING INTERROGATOR/TRANSCEIVER UNIT

RELATED APPLICATION

This application is a continuation of U.S. patent application Ser. No. 10/330,677 filed on Dec. 27, 2002, now U.S. Pat. No. 6,978,182, the entirety of which is hereby incorporated by reference.

TECHNICAL FIELD

The present disclosure relates generally to advanced patient management systems. More particularly, the present disclosure relates to advanced patient management systems including an interrogator/transceiver unit to collect, analyze, and forward data from one or more patients.

BACKGROUND

Management of patients with chronic disease consumes a significant proportion of the total health care expenditure in the United States. Many of these diseases are widely prevalent and have significant annual incidences as well. Heart failure prevalence alone is estimated at over 5.5 million patients in 2000 with incidence rates of over half a million additional patients annually, resulting in a total health care burden in excess of $20 billion. Heart failure, like many other chronic diseases such as asthma, COPD, chronic pain, and epilepsy, is event driven, where acute de-compensations result in hospitalization. In addition to causing considerable physical and emotional trauma to the patient and family, event driven hospitalizations consume a majority of the total health care expenditure allocated to the treatment of heart failure.

Hospitalization and treatment for an acute de-compensation typically occurs after the de-compensation event has happened. However, most heart failure patients exhibit prior non-traumatic symptoms, such as steady weight gain, in the weeks or days prior to the de-compensation. If the caregiver is aware of these symptoms, it is possible to intervene before the event, at substantially less cost to the patient and the health care system. Intervention is usually in the form of a re-titration of the patient's drug cocktail, reinforcement of the patient's compliance with the prescribed drug regimen, or acute changes to the patient's diet and exercise. Such intervention is usually effective in preventing the de-compensation episode and thus avoiding hospitalization.

Patients with chronic heart disease can receive implantable cardiac devices such as pacemakers, implantable cardioverter defibrillators (ICDs), and heart failure cardiac resynchronization therapy (CRT) devices. Currently, the electrophysiologist that implants pacemakers and ICDs requires their patients to make clinic visits periodically, usually once every three or four months, in order to verify if their implanted device is working correctly and programmed optimally. Device follow-ups are usually performed by the nurse-staff assisted by the sales representative from the device manufacturers. Device follow-ups are labor intensive and typically require patients to make multiple clinic visits.

The data the caregiver does receive regarding a patient requires the caregiver to analyze the data and provide predictive and post-event diagnosis based on the data. However, as the amount of data collected regarding a particular patient increases, it becomes more difficult for a caregiver to assimilate and provide a meaningful analysis of all of the data. In addition, it is difficult for a caregiver to identify trends and other information from particular patients and leverage this knowledge for the treatment of larger populations.

It would therefore be desirable to develop an automated system to collect data regarding the physiological condition of a patient, as well as collect data from implanted devices, and to automate the process of analyzing the data.

SUMMARY

The present disclosure relates generally to advanced patient management systems. More particularly, the present disclosure relates to advanced patient management systems including an interrogator/transceiver unit to collect, analyze, and forward data from one or more patients.

According to one aspect, the invention relates to an interrogator/transceiver unit in an advanced patient management system, the unit being configured to communicate with at least one device associated with a patient, and a host. The unit includes a processor module to process software instructions, an interface with a remote host, and a memory module, wherein the memory module includes, at startup, baseline software to allow the unit to ping the device and, upon a response from the device, the unit is configured to connect through the interface to the remote host to download software into the memory module that is specific to the device.

According to another aspect, the invention relates to a system for configuring an interrogator/transceiver unit for use in an advanced patient management system, the unit being configured to communicate with at least one device associated with a patient, and a host. The system includes an interrogator/transceiver unit, the unit including a processor to process software instructions, an interface, and a memory module, wherein the unit is blank at initialization, and a computer system coupled to the unit through the interface, wherein the computer system allows a user to select one or more of a plurality of device models and, upon selection, installs software associated with the selected device model on the unit.

According to yet another aspect, the invention relates to a method of transmitting data from a device associated with a patient to a remote host as part of an advanced patient management system, the method including: providing an interrogator/transceiver unit being configured to communicate with the device; initializing the unit; sending a ping from the unit to the device; and responding with identification information from the device to the unit.

According to another embodiment, the invention relates to a method of transmitting data from a device associated with a patient to a remote host as part of an advanced patient management system, the method including: providing a blank interrogator/transceiver unit; providing a computer system to allow selection from a list of a plurality of device models; selecting the device from the list of the plurality of device models; and installing software on the unit to allow the unit to communicate with the device.

The above summary is not intended to describe each disclosed embodiment or every implementation of the present invention. The figures and the detailed description which follow more particularly exemplify these embodiments.

DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present system and methods are described with respect to an advanced patient management system configured to collect patient-specific information, store and collate the information, and generate actionable recommendations to enable the predictive management of patients. The advanced patient management system is also configured to leverage a remote communications infrastructure to provide automatic device follow-ups to collect data, coordinate therapy, and to determine if remote devices are functioning properly. The term "patient" is used herein to mean any individual from whom information is collected. The term "caregiver" is used herein to mean any provider of services, such as health care providers including, but not limited to, nurses, doctors, and other health care provider staff.

Figure 1:
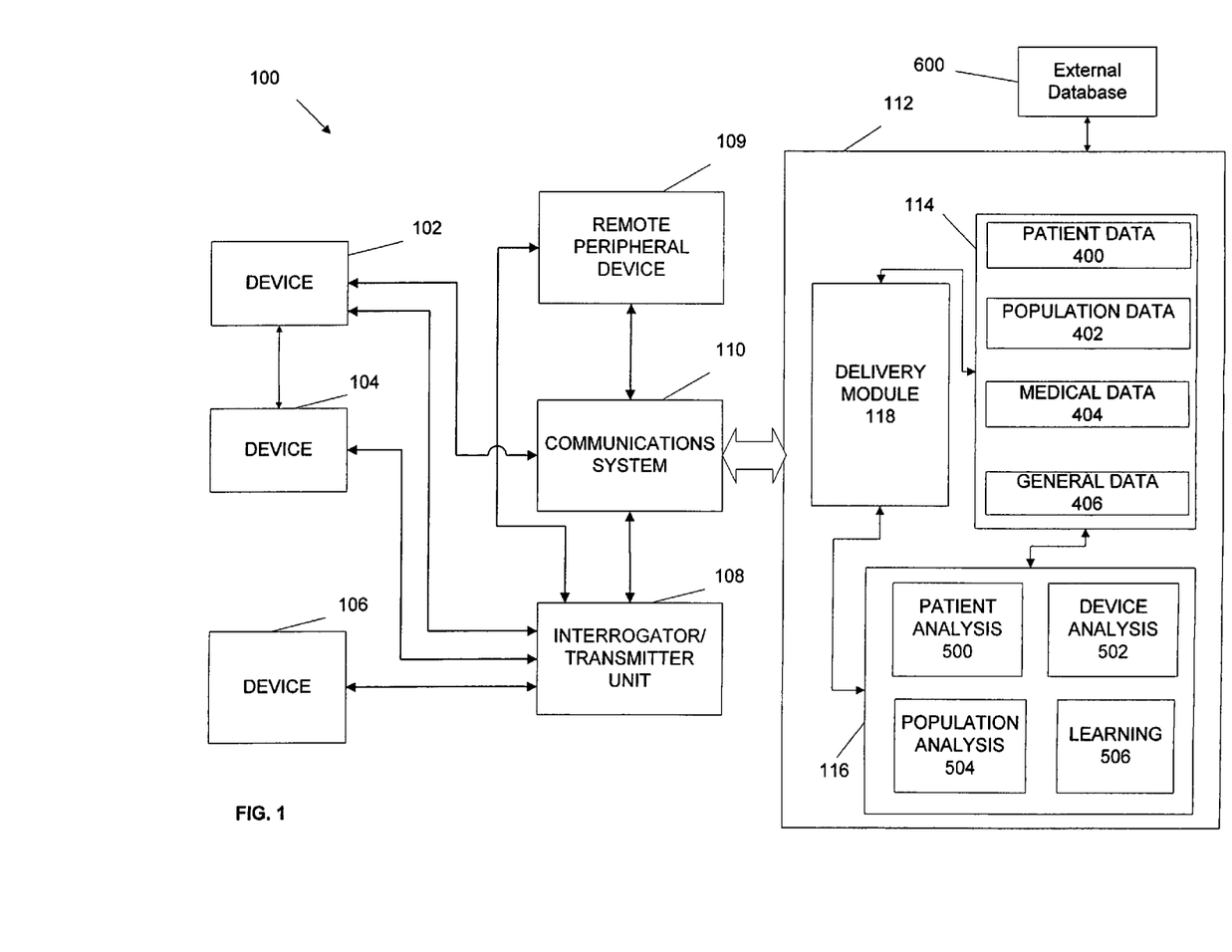
FIG. 1 illustrates an example advanced patient management system made in accordance with the present invention.

FIG. 1 illustrates an example advanced patient management system 100 made in accordance with the present invention. Advanced patient management system 100 generally includes the following components: one or more devices 102, 104, and 106, one or more interrogator/transceiver units 108, a communication system 110, one or more remote peripheral devices 109, and a host 112.

Each component of the advanced patient management system 100 can communicate using the communication system 110. Some components may also communicate directly with one another. For example, devices 102 and 104 may be configured to communicate directly with one another. The various components of the example advanced patient management system 100 illustrated herein are described below.

I. Implanted/External Devices

Devices 102, 104, and 106 can be implantable devices or external devices that may provide one or more of the following functions with respect to a patient: (1) sensing, (2) data analysis, and (3) therapy. For example, in one embodiment, devices 102, 104, and 106 are either implanted or external devices used to measure a variety of physiological, subjective, and environmental conditions of a patient using electrical, mechanical, and/or chemical means. The devices 102, 104, and 106 can be configured to automatically gather data or can require manual intervention by the patient. The devices 102, 104, and 106 can be configured to store data related to the physiological and/or subjective measurements and/or transmit the data to the communication system 110 using a variety of methods, described in detail below. Although three devices 102, 104, and 106 are illustrated in the example embodiment shown, more or fewer devices may be used for a given patient.

The devices 102, 104, and 106 can be configured to analyze the measured data and act upon the analyzed data. For example, the devices 102, 104, and 106 are configured to modify therapy or provide alarm indications based on the analysis of the data.

In one embodiment, devices 102, 104, and 106 also provide therapy. Therapy can be provided automatically or in response to an external communication. Devices 102, 104, and 106 are programmable in that the characteristics of their sensing, therapy (e.g., duration and interval), or communication can be altered by communication between the devices 102, 104, and 106 and other components of the advanced patient management system 100. Devices 102, 104, and 106 can also perform self-checks or be interrogated by the communication system 110 to verify that the devices are functioning properly. Examples of different embodiments of the devices 102, 104, and 106 are provided below.

Devices implanted within the body have the ability to sense and communicate as well as to provide therapy. Implantable devices can provide direct measurement of characteristics of the body, including, without limitation, electrical cardiac activity (e.g., a pacemaker, cardiac resynchronization management device, defibrillator, etc.), physical motion, temperature, heart rate, activity, blood pressure, breathing patterns, ejection fractions, blood viscosity, blood chemistry, blood glucose levels, and other patient-specific clinical physiological parameters, while minimizing the need for patient compliance. Derived measurements can also be determined from the implantable device sensors (e.g., a sleep sensor, functional capacity indicator, autonomic tone indicator, sleep quality indicator, cough indicator, anxiety indicator, and cardiovascular wellness indicator for calculating a quality of life indicator quantifying a patient's overall health and well-being).

Devices 102, 104, and 106 can also be external devices, or devices that are not implanted in the human body, that are used to measure physiological data (e.g., a thermometer, sphygmomanometer, or external devices used to measure blood characteristics, body weight, physical strength, mental acuity, diet, heart characteristics, and relative geographic position). Devices 102, 104, and 106 can also be environmental sensors used to measure environmental conditions (e.g., temperature, air quality, humidity, carbon monoxide level, oxygen level, barometric pressure, light intensity, and sound).

One or more of the devices 102, 104, and 106 (for example, device 106) may be external devices that measure subjective or perceptive data from the patient related to a patient's feelings, perceptions, and/or opinions, as opposed to objective physiological data. In one example embodiment, the subjective device presents the patient with a relatively small number of responses to each question posed to the patient. The responses available to the patient may include three faces representing feelings of happiness, nominalness, and sadness. Averaged over time, a trend of a patient's well being will emerge with a finer resolution than the quanta of the three responses.

The advanced patient management system 100 may also include one or more remote peripheral devices 109 (e.g., cellular telephones, pagers, PDA devices, facsimiles, remote computers, printers, video and/or audio devices) that use wired or wireless technologies to communicate with the communication system 110 and/or the host 112.

II. Interrogator/Transceiver Unit

Figure 2:
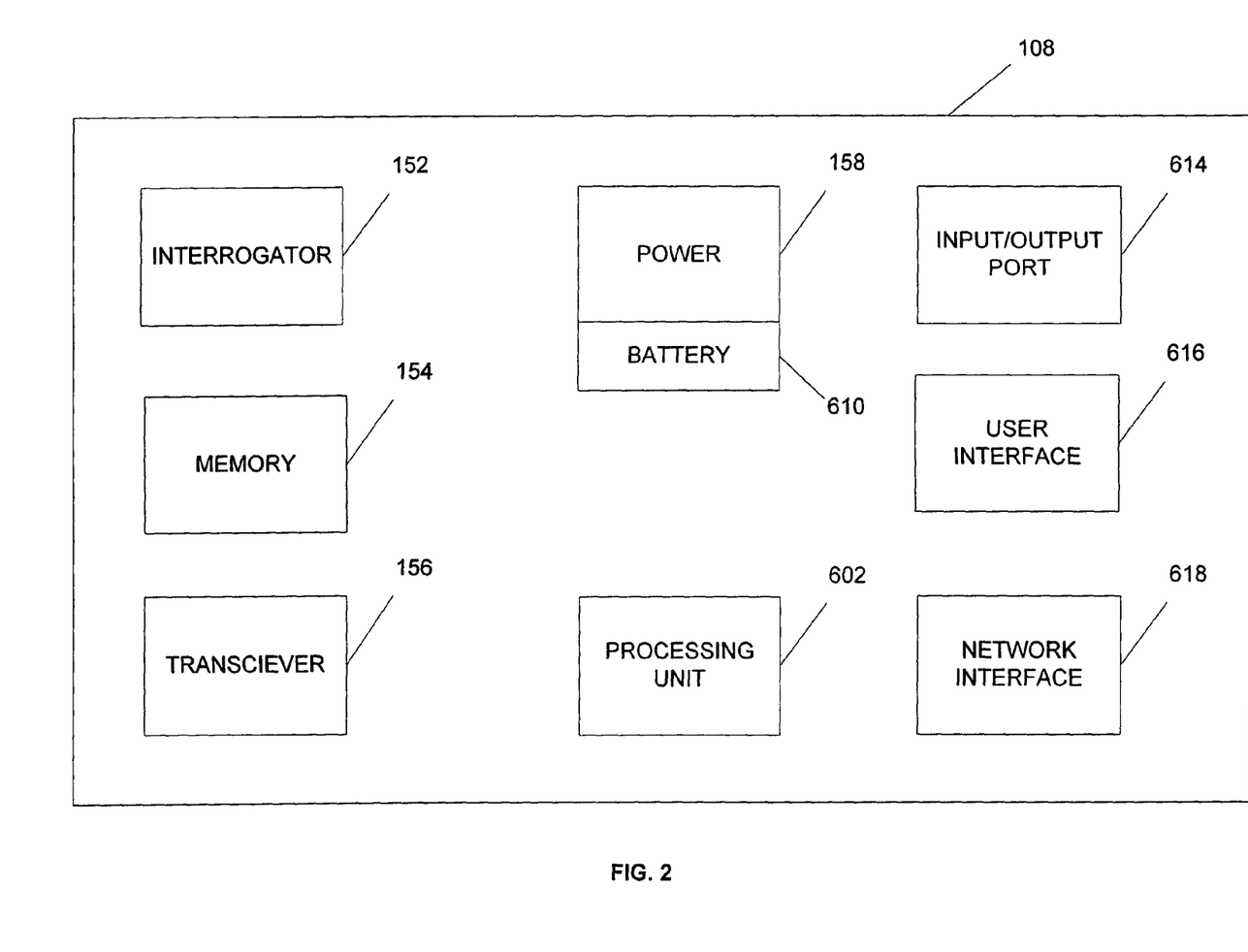
FIG. 2 illustrates an example interrogator/transceiver unit made in accordance with the present invention.

Referring now to FIG. 2, the example advanced patient management system 100 includes one or more interrogator/transceiver units ("ITUs"), such as example ITU 108. The example ITU 108 includes an interrogator module 152 for sending and receiving data from a device, such as devices 102, 104, and 106, a memory module 154 for storing data, and a transceiver module 156 for sending and receiving data to and from other components of the APM system 100. The transceiver module may operate as an interrogator of the devices 102, 104 and 106 as well. The example ITU 108 also includes a power module 158 that provides power. Further included in the ITU 108 are a processor 602, memory 606, a battery 610, an input/output port 614, a user interface 616, and a network interface 618.

The processor 602 is a typical processor for processing instructions provided in software code.

The user interface 616 allows the patient or others to communicate with the ITU 108. For example, the user interface includes one or more input devices, such as a mouse, keyboard, touch screen, microphone, etc., and one or more output devices, such as a liquid crystal display (LCD) or light emitting diode (LED), CRT screen, speaker, lights, vibrating motor, etc. The user interface 616 may be used to collect subjective data from the patient (see section I of the present application), or to provide information or alerts to the patient (see section IV of the present application).

The input/output port 614 is a typical communication port that allows the ITU 108 to connect to external devices. For example, the input/output port 614 may be a parallel, serial, or universal serial bus (USB) port to allow the ITU 108 to be connected to a computer. Other types of ports as generally known in the art may also be used.

The network interface 618 allows the ITU 108 to be connected to a network. For example, the ITU 108 may be connected to a LAN in the patient's home or directly connected to the communication system 110.

The battery 610 is part of the power module 158. The battery 610 may be rechargeable or non-rechargeable. If the battery 610 is rechargeable, the battery can be charged by using a standard battery charger, or may be charged by placing the ITU 108 in a cradle configured to accept it. In an alternative embodiment, the battery may be removed and the power module 158 can be directly connected to a standard AC power source.

The memory 154 may include any typical form of memory, such as RAM, ROM, etc. for storing data, software applications, and other electronic information. Other types of memory can also be used, such as removable memory including flash memory, microdrives, etc.

The ITU 108 performs one or more of the following functions: (1) data storage; (2) data analysis; (3) data forwarding; (4) patient interaction; (5) patient feedback; and (6) data communications. For example, the ITU 108 facilitates communications between the devices 102, 104, and 106 and the communication system 110. The ITU 108 can, periodically or in real-time, interrogate and download into memory clinically relevant patient data from the devices 102, 104, and/or 106. This data includes, in the cardiac sensor context, for example, P and R-wave measurements, pacing, shocking events, lead impedances, pacing thresholds, battery voltage, capacitor charge times, ATR episodes with electrograms, tachycardia episodes with electrograms, histogram information, and any other clinical information necessary to ensure patient health and proper device function. The data is sent to the ITU 108 by the devices 102, 104, and 106 in real-time or periodically uploaded from buffers in the devices.

The ITU 108 can be customizable and include a variety of software packages to enhance usability and compatibility. The software may control the ability of the ITU 108 to communicate with each device, as well as control the functionality of the ITU 108 itself. For example, the software allows the ITU 108 to communicate with the various devices (e.g., devices 102, 104, and 106), download data from the devices, and update configurations of the devices.

It may be advantageous to provide this functionality in software because different implanted and external devices, such as devices 102, 104, and 106, may each function and communicate differently. For example, different models of implanted pacemakers communicate with interrogators differently, and the ITU 108 must be able to communicate with each model to allow the ITU 108 to interrogate the pacemakers and successfully download desired information. It may be impractical, due to cost and size, to include memory sufficient to store the software necessary to communicate with every model of every device.

Figure 3:
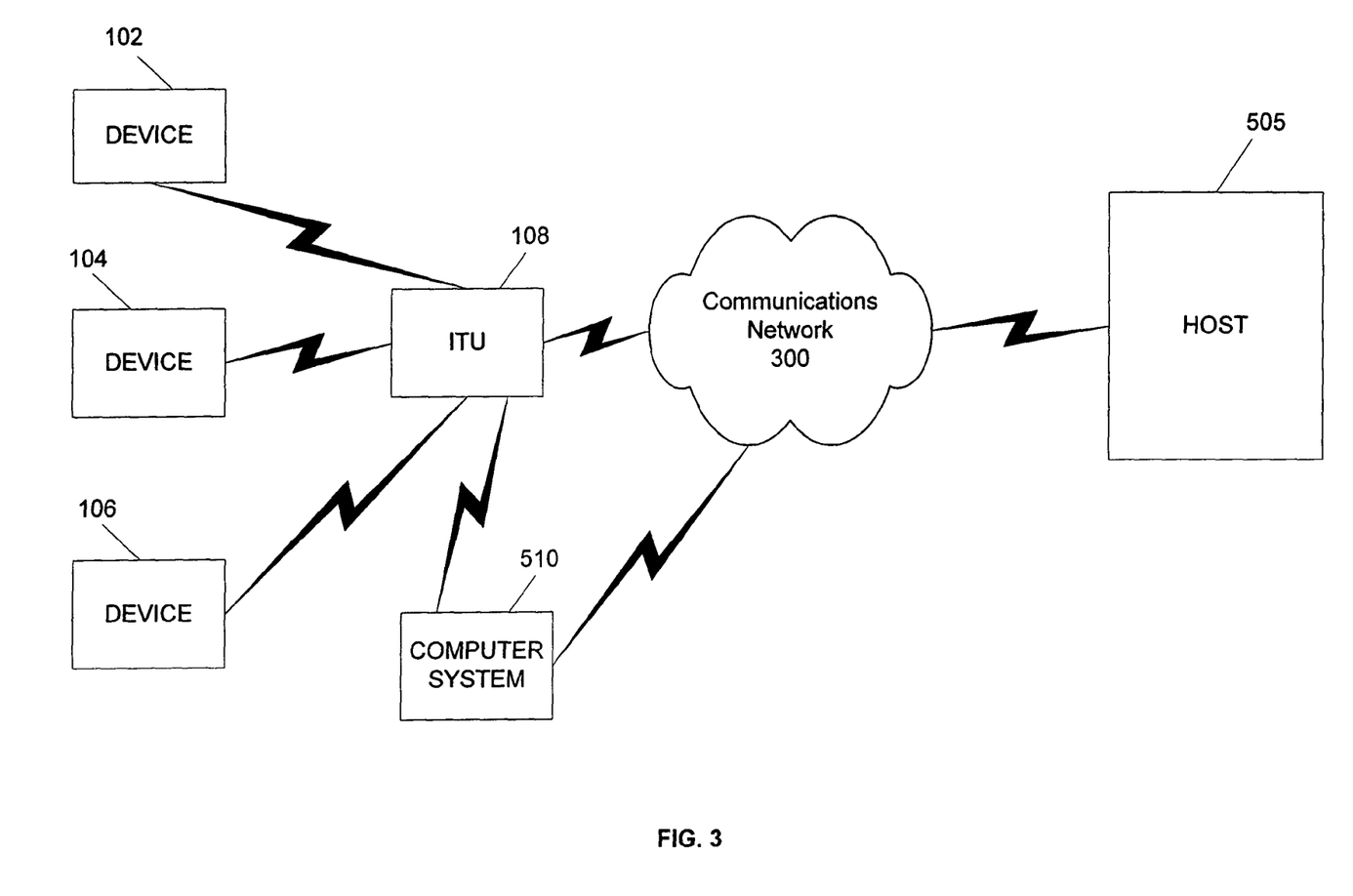
FIG. 3 illustrates an example system for updating software on an interrogator/transceiver unit.

In one embodiment shown in FIG. 3, the ITU 108 is customizable through the download of software updates from a host download source system 505. (In some embodiments, the host download source system 505 may be the same system as the host 112.) When initially taken out of the box, the ITU 108 is "blank" or includes only "baseline software." The term "blank" is used to indicate that the ITU 108 can perform initial functions such as booting up, but does not include software to allow the ITU 108 to communicate with a device. The term "baseline software" is used to indicate that the ITU includes software necessary to allow the ITU 108 to boot up and to perform generic functions such as communicating with a device at a high level. These generic functions may include the ability to send messages (e.g., ping) to devices in local proximity to the ITU to enable the ITU to determine what is in the environment surrounding the ITU, and as well as the ability to communicate with a hosting system (through, for example, the communication network 300). However, the ITU 108 with baseline software does not necessarily include software to communicate functionally with specific models of implanted or external devices.

The software necessary to allow the ITU 108 to communicate with different devices is maintained on the host download source system 505, and the software must be downloaded and installed on the ITU 108 to allow the ITU 108 to functionally communicate with the desired device or devices.

There are several methods by which the ITU 108 can download the software necessary to functionally communicate with one or more given devices. In one example method illustrated in FIG. 4, the ITU 108 includes baseline software to allow it to "ping" devices in local range of the ITU 108. A ping is a request from the ITU 108 to any devices within range to respond with identification information, such as model number, serial number, and other identifying information. Any devices in range of the ping from the ITU 108 will respond by sending back to the ITU information related to the type of device. Based on this information, the ITU 108 establishes communication with the host 505 and downloads/installs the software necessary to allow the ITU 108 to functionally communicate with the device or devices. This is an automated method for identifying and installing the needed software, and this method may be performed at initial startup of the ITU 108, as well as after a reset of the ITU 108 as desired.

Figure 5:
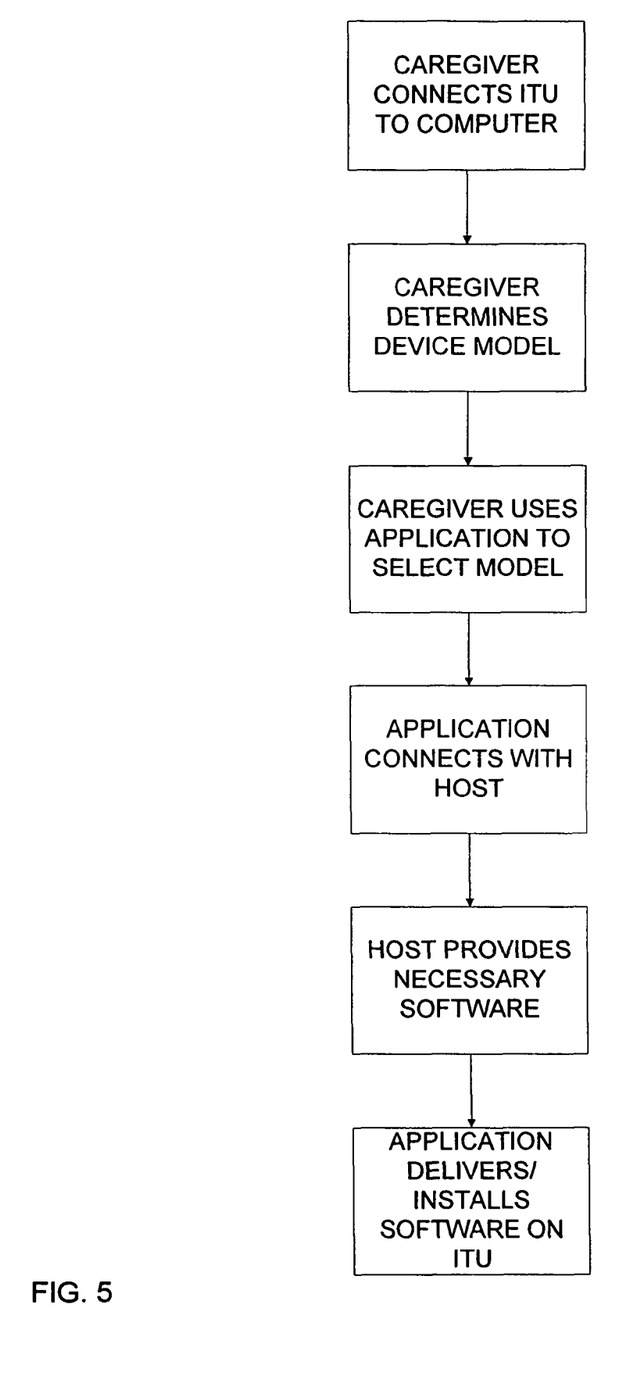
FIG. 5 illustrates an example manual method for initially updating software on an interrogator/transceiver unit.

In another example method illustrated in FIG. 5, the ITU 108 is blank and the ITU 108 is blank and is programmed by the caregiver or patient prior to use by the patient. For example, if the patient has three devices 102, 104, and 106 that are to be monitored, the caregiver uses a computer system 510 (see FIG. 3) that is networked to the host 505 (through, for example, communication network 300) to identify and download the software required for the ITU 108 to communicate with the devices 102, 104, and 106. The computer system 510 includes one or more applications to assist the caregiver in the selection of the proper software for download and installation. For example, the application on the computer system 510 may include a list of all models of a given device, and the caregiver can select the correct model and configure the desired software as needed. Once the model is selected, the application establishes a connection with the host 505 and downloads the correct software to the computer system 510. The computer system 510 and the ITU 108 are connected so that the software is then uploaded and installed on the ITU 108.

In an alternative embodiment, the software for communicating with various devices resides on the computer system 510 or a removable storage medium such as a compact disk. Therefore, once the caregiver or patient selects the appropriate device model, the software can be installed without requiring the computer system 510 to connect to the host 505.

In addition, using either the automated or manual method, the ITU 108 can be reprogrammed multiple times as desired. For example, if the ITU 108 is initially programmed to communicate with a first device, and subsequently the first device is removed and a second device is added, the ITU 108 can, automatically or manually, be reprogrammed to communicate with the second device.

Figure 4:
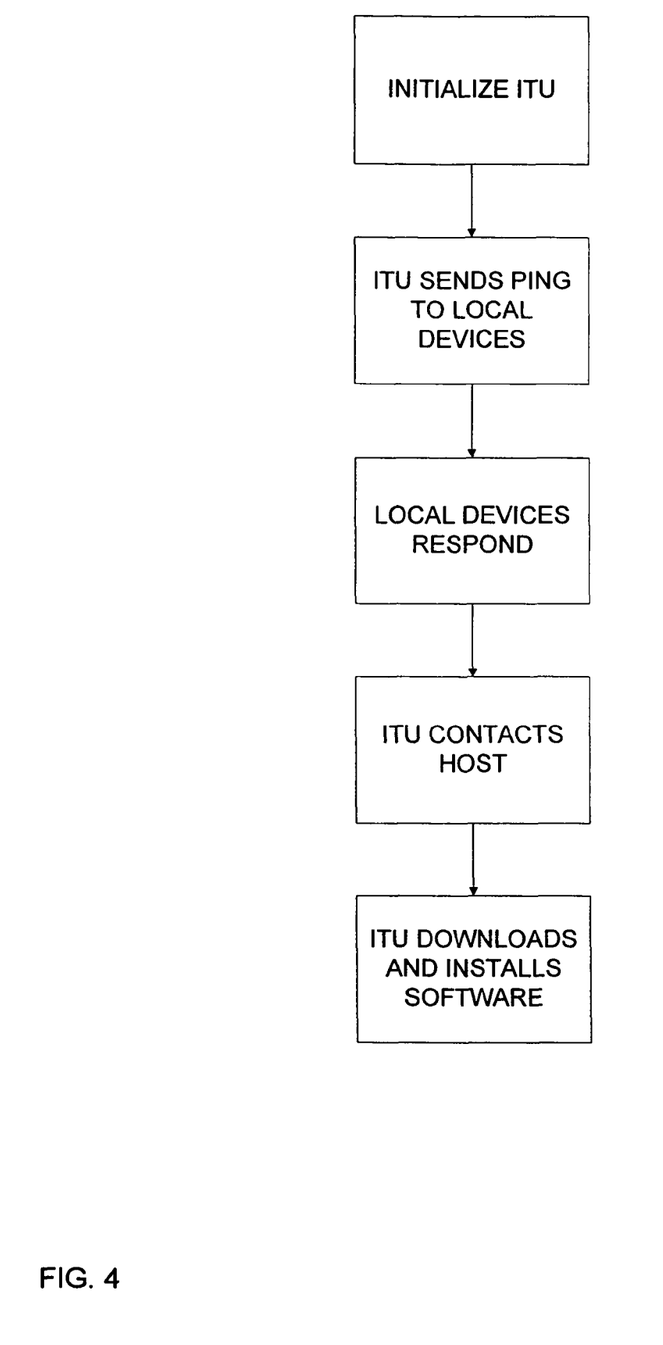
FIG. 4 illustrates an example automatic method for initially updating software on an interrogator/transceiver unit.

At the same time that the software is downloaded by either method illustrated in FIGS. 4 and 5, it is also possible to provide patient information to the host to allow data sent by the ITU 108 to the host to be properly matched with the patient (see section IV of the present application). For example, in the automated method of FIG. 4, the device provides additional information related to the patient in response to the ping, and the ITU 108 forwards this information to the host. In the manual method of FIG. 5, the caregiver or patient provides patient information at the time that the desired software is selected and downloaded from the host.

In another embodiment, the ITU 108 periodically establishes a connection with the host 505 to check if any software updates have been released. If a new version of the software is available, the ITU 108 downloads and installs the updated version.

III. Communication System

Figure 6:
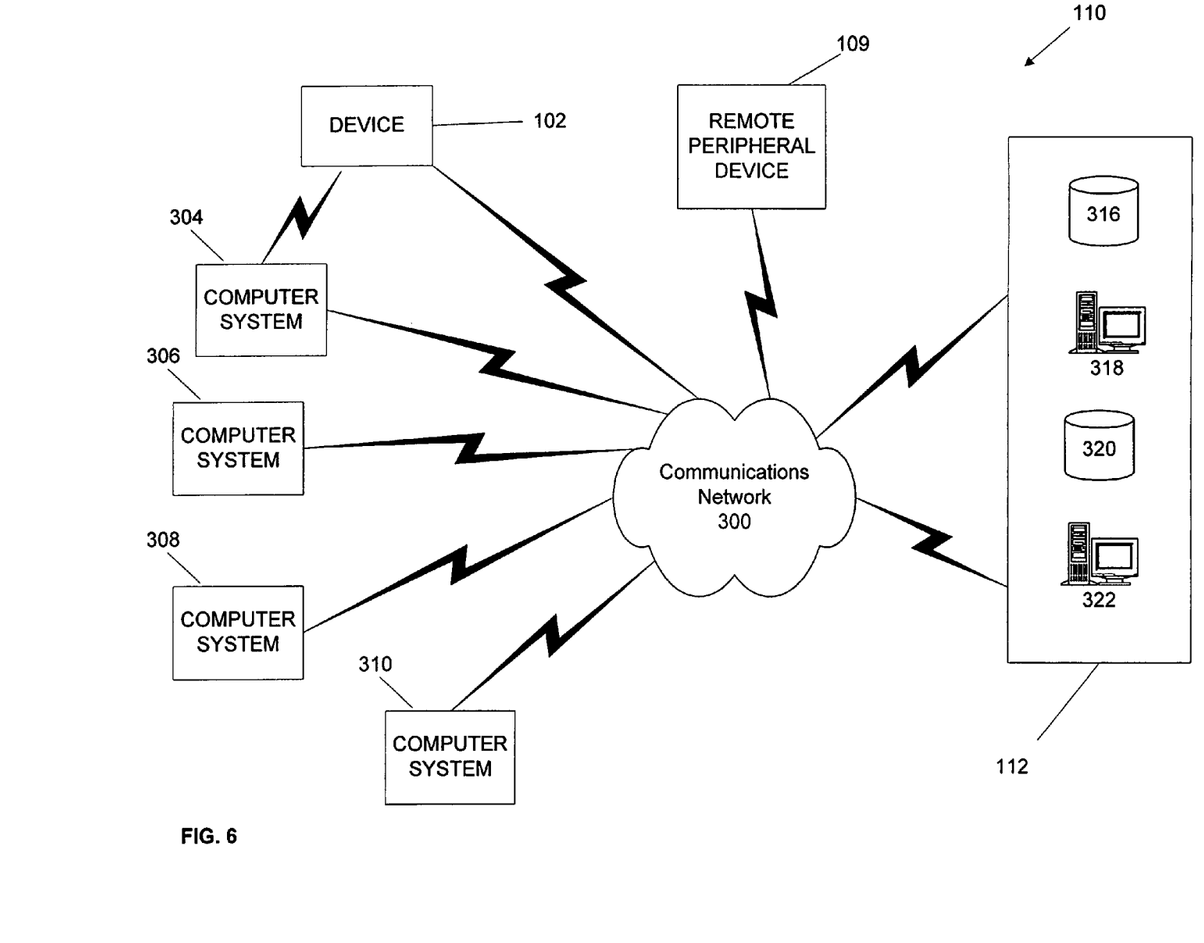
FIG. 6 illustrates an example communication system made in accordance with the present invention.

Communication system 110 provides for communications between and among the various components of the advanced patient management system 100, such as the devices 102, 104, and 106, host 112, and remote peripheral device 109. FIG. 6 illustrates one embodiment for the communication system 110 made in accordance with the present invention. The communication system 110 includes a plurality of computer systems 304, 306, 308, and 310, as well as device 102, host 112, and remote peripheral device 109, connected to one another by the communications network 300. The communications network 300 may be, for example, a local area network (LAN), wide area network (WAN), or the Internet. Communications among the various components, as described more fully below, may be implemented using wired or wireless technologies.

In the example embodiment illustrated, the host 112 includes server computers 318 and 322 that communicate with computers 304, 306, 308, and 310 using a variety of communications protocols, described more fully below. The server computers 318 and 322 store information in databases 316 and 320. This information may also be stored in a distributed manner across one or more additional servers.

A variety of communication methods and protocols may be used to facilitate communication between devices 102, 104, and 106, ITU 108, communication system 110, host 112, and remote peripheral device 109. For example, wired and wireless communications methods may be used. Wired communication methods may include, for example and without limitation, traditional copper-line communications such as DSL, broadband technologies such as ISDN and cable modems, and fiber optics, while wireless communications may include cellular, satellite, radio frequency (RF), Infrared, etc.

For any given communication method, a multitude of standard and/or proprietary communication protocols may be used. For example and without limitation, protocols such as radio frequency pulse coding, spread spectrum, direct sequence, time-hopping, frequency hopping, SMTP, FTP, and TCP/IP may be used. Other proprietary methods and protocols may also be used. Further, a combination of two or more of the communication methods and protocols may also be used.

The various communications between the components of the advanced patient management system 100 may be made secure using several different techniques. For example, encryption and/or tunneling techniques may be used to protect data transmissions. Alternatively, a priority data exchange format and interface that are kept confidential may also be used. Authentication can be implemented using, for example, digital signatures based on a known key structure (e.g., PGP or RSA). Other physical security and authentication measures may also be used, such as security cards and biometric security apparatuses (e.g., retina scans, iris scans, fingerprint scans, veinprint scans, voice, facial geometry recognition, etc.). Conventional security methods such as firewalls may be used to protect information residing on one or more of the storage media of the advanced patient management system 100. Encryption, authentication and verification techniques may also be used to detect and correct data transmission errors.

Communications among the various components of the advanced patient management system 100 may be enhanced using compression techniques to allow large amounts of data to be transmitted efficiently. For example, the devices 102, 104, and 106 or the ITU 108 may compress the recorded information prior to transmitting the information to the ITU 108 or directly to the communication system 110.

The communication methods and protocols described above can facilitate periodic and/or real-time delivery of data.

IV. Host

The example host 505 (see FIG. 3) is configured to receive a request for software from the ITU 108 or computer system 510 and to upload the software to the ITU 108 or computer system 510. Specifically, the host 505 may comprise one or more databases to house software necessary to communicate with a plurality of different devices. Upon receiving a request for software from the ITU 108, the host 505 queries one or more databases and identifies the correct software for the selected device model or models. This software is made available for the ITU 108 or computer system 510 to download. The host 505 may also perform other functions, such as to automatically push software updates down to the ITU 108 as needed.

The host 505 may be a part of the example host 112 (see FIG. 1). The host 112 includes a database module 114, an analysis module 116, and a delivery module 118. Host 112 preferably includes enough processing power to analyze and process large amounts of data collected from each patient, as well as to process statistics and perform analysis for large populations. For example, the host 112 may include a mainframe computer or multi-processor workstation. The host 112 may also include one or more personal computer systems containing sufficient computing power and memory. The host 112 may include storage medium (e.g., hard disks, optical data storage devices, etc.) sufficient to store the massive amount of high-resolution data that is collected from the patients and analyzed.

The host 112 may also include identification and contact information (e.g., IP addresses, telephone numbers, or a product serial number) for the various devices communicating with it, such as ITU 108 and peripheral device 109. For example, each ITU 108 is assigned a hard-coded or static identifier (e.g., IP address, telephone number, etc.), which allows the host 112 to identify which patient's information the host 112 is receiving at a given instant. Alternatively, each device 102, 104, and 106 may be assigned a unique identification number, or a unique patient identification number may be transmitted with each transmission of patient data.

When a device is first activated, several methods may be used to associate data received by the advanced patient management system 100 with a given patient. For example, each device may include a unique identification number and a registration form that is filled out by the patient, caregiver, or field representative. The registration form can be used to collect the necessary information to associate collected data with the patient. Alternatively, the user can logon to a web site to allow for the registration information to be collected. In another embodiment, a barcode is included on each device that is scanned prior to or in conjunction deployment of the device to provide the information necessary to associate the recorded data with the given patient.

Referring again to FIG. 1, the example database module 114 includes a patient database 400, a population database 402, a medical database 404, and a general database 406, all of which are described further below. The patient database 400 includes patient specific data, including data acquired by the devices 102, 104, and 106, as well as a patient's medical records and historical information. The population database 402 includes non-patient specific data, such as data relating to other patients and population trends. The example medical database 404 includes clinical data relating to the treatment of diseases, such as historical trend data for multiple patients in the form of a record of progression of their disease(s) along with markers of key events. The general database 406 includes non-medical data of interest to the patient, such as information relating to news, finances, shopping, technology, entertainment, and/or sports.

In another embodiment, information is also provided from an external source, such as external database 600. For example, the external database 600 includes external medical records maintained by a third party, such as drug prescription records maintained by a pharmacy, providing information regarding the type of drugs that have been prescribed for a patient.

The example analysis module 116 includes a patient analysis module 500, device analysis module 502, population analysis module 504, and learning module 506. Patient analysis module 500 may utilize information collected by the advanced patient management system 100, as well as information for other relevant sources, to analyze data related to a patient and provide timely and predictive assessments of the patient's well-being. Device analysis module 502 analyzes data from the devices 102, 104, and 106 and ITU 108 to predict and determine device issues or failures. Population analysis module 504 uses the data collected in the database module 114 to manage the health of a population. Learning module 506 analyzes the data provided from the various information sources, including the data collected by the advanced patient system 100 and external information sources, and may be implemented via a neural network (or equivalent) system to perform, for example, probabilistic calculations.

Delivery module 118 coordinates the delivery of feedback based on the analysis performed by the host 112. For example, based on the data collected from the devices and analyzed by the host 112, the delivery module 118 can deliver information to the caregiver or to the patient using, for example, a display provided on the ITU 108.

One or more headings have been provided above to assist in describing the various embodiments disclosed herein. The use of headings, and the resulting division of the description by the headings, should not be construed as limiting in any way. The subject matter described under one heading can be combined with subject matter described under one or more of the other headings without limitation and as desired.

The systems and methods of the present disclosure can be implemented using a system as shown in the various figures disclosed herein including various devices and/or programmers, including implantable or external devices. Accordingly, the methods of the present disclosure can be implemented: (1) as a sequence of computer implemented steps running on the system; and (2) as interconnected modules within the system. The implementation is a matter of choice dependent on the performance requirements of the system implementing the method of the present disclosure and the components selected by or utilized by the users of the method. Accordingly, the logical operations making up the embodiments of the method of the present disclosure described herein can be referred to variously as operations, steps, or modules. It will be recognized by one of ordinary skill in the art that the operations, steps, and modules may be implemented in software, in firmware, in special purpose digital logic, analog circuits, and any combination thereof without deviating from the spirit and scope of the present invention as recited within the claims attached hereto.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification.

What is claimed is:

1. An interrogator/transceiver unit, the unit comprising:
a processor module programmed to process software instructions;
an interface module programmed to communicate with an implantable device associated with a patient and also programmed to communicate with a remote host, where the implantable device is local to the unit; and
a memory module, wherein the memory module includes baseline software that enables the unit to identify the device,
wherein the unit is configured to:
use the baseline software to obtain identification information from the implantable device,
communicate with the remote host to download, into the memory module of the unit, device-specific software that is selected by the remote host using the identification information received by the unit from the implantable device, and configure the unit with the device-specific software to communicate with the implantable device.

2. The unit of claim 1, wherein the unit is configured to automatically communicate, using the baseline software, with one or more devices that are near the unit.

3. The unit of claim 1, wherein the unit is configured to automatically communicate with the remote host to download the device management software.

4. The unit of claim 3, wherein the identification information received by the unit from the implantable device includes an indication of a model of the implantable device, and wherein the unit is configured to communicate information about the model to the remote host.

5. The unit of claim 1, wherein the unit is configured to recurrently communicate with the remote host to download updated device management software to the memory module of the unit.

6. The unit of claim 1, wherein the identification information from the implantable device includes an indication of a model of the implantable device, and wherein the unit is configured to communicate information about the model to the remote host.

7. The unit of claim 6, wherein the identification information from the implantable device includes a model number and a serial number of the device.

8. The unit of claim 1, wherein using the baseline software to obtain identification information, communicate with the remote host, and configure the unit with device-specific software occurs upon reset of the unit.

9. A system comprising:

an external interrogator/transceiver unit configured to communicate with an implanted device associated with a patient and with a remote host; and a computer system, located local to the external interrogator/transceiver and capable of communicating with the unit, wherein the computer system is configured to:

allow a user to select one or more of a plurality of device models associated with the device, upon selection, communicate with the remote host to download the device-specific software associated with the one or more selected device models, wherein the remote host is configured to select the device-specific software associated with the one or more selected device models; and install on the unit, the device-specific software to allow the unit to communicate with the device.

10. The system of claim 9, wherein the unit is further configured to:

communicate with the implantable device to obtain patient information; and communicate the patient information to the remote host substantially simultaneously with the communication from the computer system to the remote host to download the device-specific software associated with the one or more selected device models.

11. A method of transmitting data from a device associated with a patient to a remote host, the method comprising:

detecting one or more devices in local proximity;

pinging each detected device to obtain identification information;

retrieving device management software for each device from the remote host, the retrieving including communicating the identification information to the remote host for selecting appropriate device management software;

installing the device management software on an external unit in local proximity to the devices; and using the device management software to functionally communicate between the unit and each device.

12. The method of claim 11, wherein the detecting the one or more devices is performed using baseline software on the unit.

13. The method of claim 11, wherein the identification information includes at least one of a model number and a serial number of the device.

14. The method of claim 11, wherein detecting the one or more devices in local proximity is performed after resetting the unit.

* * * * *

UNITED STATES PATENT AND TRADEMARK OFFICE
CERTIFICATE OF CORRECTION

PATENT NO. : 7,751,901 B2  Page 1 of 1
APPLICATION NO. : 11/259938
DATED : July 6, 2010
INVENTOR(S) : Scott T. Mazar et al.

It is certified that error appears in the above-identified patent and that said Letters Patent is hereby corrected as shown below:

On the title page, item (57), under "Abstract", in column 2, line 7, delete "facility" and insert -- facilitate --, therefor.

Signed and Sealed this

Thirty-first Day of August, 2010

David J. Kappos
*Director of the United States Patent and Trademark Office*